United States Patent [19]

Liu et al.

[11] Patent Number: 4,499,317

[45] Date of Patent: Feb. 12, 1985

[54] MODIFIED ZEOLITE CATALYST COMPOSITION AND PROCESS FOR ALKYLATING TOLUENE WITH METHANOL TO FORM STYRENE

[75] Inventors: Huei-Cheng Liu, Oakland; Ralph J. Spohn, Woodcliff Lake, both of N.J.

[73] Assignee: Exxon Research & Engineering Co., Florham Park, N.J.

[21] Appl. No.: 627,339

[22] Filed: Jul. 2, 1984

Related U.S. Application Data

[62] Division of Ser. No. 487,585, Apr. 22, 1983.

[51] Int. Cl.$^3$ .............................................. C07C 1/20
[52] U.S. Cl. .................................. 585/438; 585/437; 585/469
[58] Field of Search ............... 585/437, 438, 428, 469; 502/73, 79

[56] References Cited

U.S. PATENT DOCUMENTS

| | | | |
|---|---|---|---|
| 3,251,897 | 5/1966 | Wise et al. | 502/79 |
| 4,115,424 | 9/1978 | Unland et al. | 585/438 |
| 4,140,726 | 2/1979 | Unland et al. | 585/438 |
| 4,429,174 | 1/1984 | Teng et al. | 502/79 |
| 4,463,204 | 7/1984 | Liu | 585/437 |

FOREIGN PATENT DOCUMENTS 57-68144  4/1982  Japan .................................. 585/438

OTHER PUBLICATIONS

Itoh et al., J. Catalysis 72, 170 (1981).
Yashima et al., J. Catalysis, 26, 303 (1972).
Sidorenko et al., Dokl. Akad. Nauk SSSR 173, 132 (1967).
Sodesawa et al., B. Chem. Soc. Japan, 52, 2431 (1979).
Sherry, J. Phys, Chem., 70, 1158 (1966).

*Primary Examiner*—Delbert E. Gantz
*Assistant Examiner*—A. Pal
*Attorney, Agent, or Firm*—Robert A. Maggio

[57] ABSTRACT

A modified zeolite catalyst composition and process for using the catalyst composition to alkylate toluene (or derivative thereof) with methanol to form e.g. styrene and ethylbenzene (or derivatives thereof) is disclosed. The catalyst composition is exemplified by a type X- or Y-zeolite modified with (1) at least one alkali metal selected from Cs, K, and Rb; (2) at least one metal selected from Mn, Fe, Cu, and Zn; and (3) boron and/or phosphorus.

21 Claims, No Drawings

MODIFIED ZEOLITE CATALYST COMPOSITION AND PROCESS FOR ALKYLATING TOLUENE WITH METHANOL TO FORM STYRENE

This is a division of application Ser. No. 487,585, filed Apr. 22, 1983.

BACKGROUND OF THE INVENTION

The present invention is directed to catalyst compositions and processes for reacting toluene and methanol to form styrene.

Styrene is currently commercially produced from benzene in a two-step process. In the first step benzene is alkylated with ethylene to form ethylbenzene, and in the second step, the ethylbenzene is dehydrogenated to form styrene.

For example, the alkylation of aromatic compounds with olefins, alkyl halides and alcohols in the presence of a rare earth metal (including cerium) modified X- or Y-type zeolite is broadly disclosed in U.S. Pat. No. 3,251,897. Such alkylations are non-specific to styrene, the predominant reaction disclosed being benzene+ethylene to form ethylbenzene. Thus, such zeolite catalyzed reactions can be employed to make ethylbenzene in the first stage of conventional styrene synthesis.

One of the known alternative routes for forming styrene involves the oxidative coupling of toluene to form 1,2-diphenyl ethylene (stilbene) followed by the disproportionation of the stilbene with ethylene in the presence of a catalyst to form styrene. The economic significance of the overall process scheme of the toluene-stilbene route resides in the fact that styrene can be produced from 0.5 mole of ethylene and one mole of toluene. This compares with the conventional ethylbenzene route wherein styrene is produced from one mole of ethylene and one mole of benzene.

In light of the rising costs of benzene and ethylene and the environmental problems of benzene, toluene-based processes will become a more attractive route than the existing benzene-based process for styrene manufacture.

Representative catalysts employed in the toluene to stilbene route are metal oxides such as those disclosed in U.S. Pat. Nos. 3,694,518; 3,739,038; 3,868,427; 3,965,206; 3,980,580; 4,091,044; 4,183,828; 4,243,825; 4,247,727; 4,254,293; 4,255,602; 4,255,603; 4,255,604; 4,268,703; 4,268,704, 4,278,824; 4,278,825; and 4,278,826 all assigned to Monsanto.

Commonly assigned U.S. patent application Ser. No. 405,603, filed Aug. 6, 1982 by H. Teng and I. Huang employs a faujasite zeolite modified with Li, K, Rb or cesium cations and at least one promoter selected from the group consisting of B, P, Pb, Cu, Zn, Ni, O, and Fe for the toluene to stilbene route.

A separate and distinct alternative route to styrene from toluene involves the alkylation of the side chain of toluene with methanol or formaldehyde by contact of these reactants with X- and Y-type zeolites, as described in Yashima et al in the Journal of Catalysis, Vol. 26, 303-312 (1972). More specifically, it is disclosed therein that alkylation of the methyl group of toluene to form styrene and ethylbenzene is effected by Na, K, Rb or Cs exchanged X- or Y-type zeolites, whereas Li exchanged zeolites of the same type effected predominantly alkylation of the benzene ring of toluene to form xylenes. Yashima et al interpret their results as suggesting that xylene formation is attributable to the acidity of the catalyst, whereas styrene and ethylbenzene formation is attributable to the basicity of the catalyst.

Sidorenko et al in the article "Condensation of Toluene and Methanol on Synthetic Zeolites Exchanged with Alkali Ions", Dokl. Akad. Nauk SSSR, Vol. 173 No. 1:132-34 (1967), have proposed a mechanism for the alkylation of toluene with methanol using alkali metal exchanged X- and Y-type zeolites wherein methanol is converted to formaldehyde which then reacts with toluene to produce styrene and ethylbenzene.

However, since alkali metal exchanged zeolites are capable of catalyzing a variety of reactions and therefore produce a variety of by-products, the selectivity of the toluene to styrene is very low when conducting the process in accordance with Yashima et al or Sidorenko et al.

Furthermore, the commercial attractiveness of the toluene/methanol alkylation reaction is contingent upon achieving a sufficiently high selectivity to styrene relative to ethylbenzene to reduce the cost of dehydrogenating ethylenebenzene to styrene.

In an effort to improve the selectivity of the toluene/methanol alkylation reaction to styrene, Unland et al, U.S. Pat. No. 4,140,726 describe the use of an X- or Y-type zeolite which has been modified by a cation exchange with one or more of potassium, rubidium and cesium and impregnated with boron or phosphorus. While toluene to methanol mole ratios in the feed are disclosed as varying from 0.5:1 to 20:1 (Col. 2, Lines 20 et seq) it is disclosed to be desirable to employ excess toluene in the feed relative to methanol to minimize side reactions which decompose methanol, and in fact the data reported in the examples employ toluene:methanol ratios of at least 5:1. Conversions and selectivities are reported on the basis of methanol in the feed. A disadvantage is associated with maintaining the methanol concentration in the feed substantially below the toluene concentration, namely, the effective toluene conversion per pass at a toluene:methanol mole ratio of 5:1 is necessarily not greater than 20% of the methanol conversion for stoichiometric reasons and in this patent can be calculated to be 6.7% (Example 1, Col. 6, Line 5). Toluene is more expensive than methanol, and ideally one would want to maximize toluene conversion and avoid or minimize recycling of the toluene. To do this, however, the methanol concentration in the feed must be increased. Recycle of methanol relative to toluene is a much simpler procedure and due to the cost of methanol such recycle may even be dispensed with altogether. If one attempts to improve toluene conversion by increasing the methanol concentration in the feed when employing the Unland et al catalysts, however, the styrene selectivity ratio, i.e. the ratio of styrene to styrene+ethylbenzene on a mole percentage basis, is reduced as described hereinafter in the Comparative Example. Thus, when using the Unland et al catalysts one is forced to accept a substantial reduction in the styrene selectivity ratio for increases in toluene conversions induced by increases in the methanol concentration.

Itoh et al report in J. of Catalysis, Vol. 72, p. 170 (1981) the use of Rb, K, Li cation exchanged X-type zeolites, such as Rb Li-X, Rb-X and RbK-X, for the side chain alkylation of p-xylene with methanol to produce p-methylstyrene and p-ethyltoluene. A maximum 68 mole % conversion of methanol with mole % yields of 5.3% (p-methyl styrene) and 2.7% (p-ethyltoluene) are disclosed. Use of Cs and/or Li exchange in conjunction with B and/or P impregnated zeolites is not disclosed nor the effects obtainable therefrom.

Japanese Patent Application Publication No. Sho 57-68144 published Apr. 26, 1982 is directed to catalyst for styrene synthesis which comprises a zeolite of the faujasite class having at least 20% of the sodium cations present therein exchanged with cesium, potassium or rubidium and which has been treated to impregnate therein one or more divalent or trivalent metal salts of boric or phosphoric acid, the metal of said salt disclosed as being selected from magnesium, calcium, aluminum, manganese, iron, cobalt, nickel, copper and zinc.

The search has continued for catalyst compositions capable of improving the conversion and/or styrene selectivity of toluene side chain alkylation reactions with methanol. The present invention was developed in response to this search.

SUMMARY OF THE INVENTION

One aspect of the present invention provides a catalyst composition capable of catalyzing the side chain alkylation of toluene with methanol comprising a crystalline aluminosilicate zeolite of the faujasite structure with a $SiO_2:Al_2O_3$ mole ratio of from about 2 to about 8 and having present therein (1) at least one alkali metal selected from the group consisting of Cs, K, and Rb; (2) at least one metal selected from the Group of M metals consisting of Mn, Fe, Cu, and Zn; and (3) at least one member selected from the group consisting of boron and phosphorus.

Another aspect of the present invention provides a process for alkylating toluene or toluene derivative with an alkylating agent, e.g., methanol, which comprises reacting the alkylating agent with at least one compound represented by the structural formula:

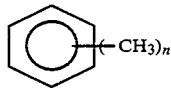
(I)

wherein n is a number which can vary from 1 to 6. The reaction is conducted in the presence of the aforedescribed zeolite catalyst composition and under conditions and in a manner sufficient to form a product comprising at least one compound represented by the structural formulae:

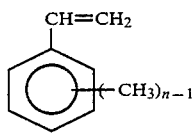
(II)

and

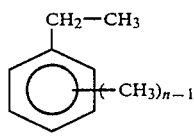
(III)

wherein n is a number which corresponds in value to that employed for n in structural formula I above. Preferably the product comprises a compound represented by structural formula I.

Methylations of toluene with methanol can produce some methanol decomposition products, and over certain conventional catalysts are capable of producing various xylenes or other alkylated aromatics, as well as some polymer, aromatization and coke materials, along with the styrene and ethylbenzene sought in the process of the present invention. The present invention provides a means of directing the process toward the production of styrene and ethylbenzene (or derivatives thereof when employing toluene derivatives in the feed), and to particularly toward styrene. The use of the catalysts of the present invention increases the selectivity and/or yield to styrene, i.e., the ratio of styrene to styrene plus ethylbenzene is enhanced in the product, relative to the use of a catalyst lacking one or more of the three required components discussed herein. Both styrene and ethylbenzene are useful products and sought in the present invention. However, the usual use for ethylbenzene is to prepare styrene by dehydrogenation, and therefore styrene is the more valuable product. Accordingly, the capability of directing the process of the present invention toward styrene at the expense of ethylbenzene is an advantage thereof. This advantage stems, in part, from the fact that as the styrene selectivity increases, the cost of high temperature dehydrogenation of ethylbenzene is reduced along with the size and cost of towers needed to separate ethylbenzene from styrene. Furthermore, the enhancement of styrene selectivity and/or yield is obtainable at higher methanol concentrations in the feed and hence higher toluene conversions, relative to the lower methanol concentrations conventionally employed in reactions of this type with conventional catalysts. This advantage further enhances the cost savings by decreasing feed component recycle costs as described above.

DESCRIPTION OF PREFERRED EMBODIMENTS

In accordance with the process of the present invention toluene or a toluene derivative is contacted with methanol in the presence of a catalyst composition comprising zeolite catalysts modified with selected materials to form styrene.

More specifically, zeolites, which are crystalline in nature, are known for the alkylation of toluene to styrene and ethylbenzene. It has been found that such zeolites can be modified as taught herein to provide improved catalysts for such reactions. For example, the X- or Y-type zeolites described in U.S. Pat. Nos. 3,251,897 and 4,140,726, as well as those described in the Journal of Catalysis, Yashima et al, Vol. 26, 303–312 (1972) may be employed as described herein.

In general, suitable zeolites which can be modified in accordance with the present invention preferably will be of the faujasite structure with a $SiO_2:Al_2O_3$ mole ratio in the range of about 2 to about 8. With regard to structural classification, those zeolites with a double 6-ring, or faujasite structure, are generally suitable for use herein. Such zeolites characteristically have pore diameters of at least 6 angstroms, preferably at least 8 angstroms (e.g. 6 to 15 angstroms), which is appropriate for admission of toluene and derivatives thereof, and to allow exit of styrene and ethylbenzene. The X- and Y-type zeolites have been found very suitable for modification and use herein, with the X-type being particularly preferred.

Type-X zeolite can be represented in terms of mole ratios of oxides as follows:

$$1.0\pm0.2Z_{2/n}O:Al_2O_3:2.5\pm0.5SiO_2:YH_2O$$

wherein Z is a cation having a valence of not more than 3, n represents the valence of Z, and Y is a value up to 8, depending on the identity of Z and the degree of hydration of the crystal. The sodium form may be represented in terms of mole ratios of oxides as follows:

$$Na_2O:Al_2O_3:2.5SiO_2:6H_2O$$

although the mole ratio of $SiO_2:Al_2O_3$ can typically vary from about 2:1 to about 3:1. Zeolite-X is commercially available in both the sodium and the calcium forms; the former being preferred for the purpose of the invention.

Zeolite Y differs from zeolite X in that it contains more silica and less alumina. Consequently, due to its higher silica content this zeolite has more stability to the hydrogen ion than zeolite X.

The sodium form of zeolite Y, which is preferred for use herein is represented in terms of mole ratios of oxides as follows:

$$0.9\pm0.2Na_2O:Al_2O_3:WSiO_2:XH_2O$$

wherein "W" is a number having a value of typically from about 3 to about 8 preferably 3 to about 6 and "X" is a number having a value up to about 9.

The selectivity of zeolite Y for larger molecules is appreciably the same as zeolite X because its pore size extends from 10 to 13 angstrom units.

Type L zeolites and natural faujasite materials are examples of other zeolites having appropriate pore size and structure for use herein. In general, zeolites having suitable properties can be utilized, whether obtainable as natural materials or prepared synthetically, and can be obtained from commercial sources or prepared by appropriate laboratory crystallization procedures.

The zeolites described hereinabove are modified to have present therein (1) at least one alkali metal, preferably cations of said alkali metal, selected from the group consisting of Cs, K, and Rb, e.g., which is chemisorbed and/or ionically bonded to the zeolite; preferably at least Cs (e.g. cesium cation) is incorporated into the zeolite with or without K, and Rb; (2) at least one metal (M), preferably cations of at least one of said metals (M), selected from the group consisting of Mn, Fe, Cu, and Zn, said metals M being referred to herein collectively or individually as Group M metal(s) for ease of discussion; and (3) boron and/or phorphorus, preferably boron and phosphorus. Dehydration of the zeolite, e.g. by calcination, produces the characteristic system of open pores, passages or cavities of crystalline aluminosilicates.

Since Cs, K, Rb, and the Group M metals can exist as cations, they are most conveniently incorporated into the zeolite by conventional ion exchange procedures using a fluid medium to partially replace therewith, the sodium, hydrogen or other cations normally present in the zeolite. Any medium which will ionize the cation without affecting the ultimate crystalline structure of the zeolite may be employed for exchange. Heating of the exchange solution to temperatures of from about 80° to about 100° C. is preferred to facilitate the rate of ion exchange. Typically, aqueous and/or organic, preferably aqueous, solutions of the alkali metals, e.g., Cs, and/or Group M metals are employed for this purpose, although zeolites prepared directly with the appropriate cations present therein may be employed. Metal compounds which can be solubilized in aqueous or organic media for ion exchange include alkali and Group M metal; halides, hydroxides, nitrates, acetates, and mixtures thereof.

In addition to water, any organic medium, preferably a volatile organic medium, which permits impregnation, preferably ion exchange, of said alkali metal, e.g., Cs, and Group M metals can be employed, including such organic solvents as alcohols, ketones, ethers, amides and other polar organic solvents, and mixtures thereof.

Representative of such organic solvents include acetone, methanol, ethylene glycol, isopropanol, isobutanol, diethylether, benzene, toluene, dimethyl formamide, tetrahydrofuran, methylethyl ketone, methylbutyl ketone, and mixtures thereof.

Incorporation of the boron and/or phosphorus components is conducted by any method of contacting the same with the zeolite which results in retention, e.g., by chemisorption, ionic bonding, physical adsorption and/or the like, of these impregnants in the zeolite, and various compounds and procedures are suitable for this purpose. Thus, the B and/or P components can conveniently be incorporated into the zeolite by inclusion in an ion exchange solution, or by subsequently utilizing a solution of such component as a slurrying medium for zeolite particles or as an impregnating medium to be absorbed in the zeolite. The medium for incorporating the B and/or P does not necessarily have to completely dissolve these impregnants, and in fact may often contain suspended solids. Solutions or slurries of the B and/or P components in the aforedescribed solutions, e.g., suitable for the alkali and Group M metal incorporation, can be employed.

Representative sources of the B and/or P components for use in impregnation include potassium tetraborate ($K_2B_4O_7$ in hydrated or anhydrous form), sodium tetraborate ($Na_2B_4O_7$ in hydrated or anhydrous form), boric oxide ($B_2O_3$), boric acid ($H_3BO_3$), borate esters, such as trimethyl borate, tri-n-butyl borate, tricyclohexylborate, boron phosphate ($BPO_4$), boron phosphide (BP), borate ethers, such as trimethoxyborine ($(CH_3O)_3B$, phosphoric acid and its esters, such as trimethyl phosphate ($(CH_3O)_3PO$), potassium phosphate ($K_3PO_4$), and mixtures thereof.

An aqueous solution of boron phosphate is preferred because the boron exists as a cation in this compound which can be readily exchanged.

While the sequence of incorporation of the alkali metal(s) (Cs, K, Rb), Group M metals, and B and/or P into the zeolite is not critical, it is preferred to incorporate the various components in the following general order: alkali metal; B and/or P; Group M metal. The alkali metal is incorporated into the zeolite in an amount effective to enhance the selectivity to styrene and ethylbenzene relative to its absence.

In theory, 81% of sodium on type X and 71% of the sodium of type Y zeolites is exchangeable. Effective amounts of the alkali metal cation can be incorporated by exchanging typically from about 20 to about 65, preferably from about 40 to about 65, and most preferably from about 50 to about 65% or higher by weight of the sodium cations for the alkali metal cation.

Accordingly, when cesium is employed as the alkali metal, the modification is typically conducted to impart a cesium content (e.g. by exchange) to the zeolite of typically from about 10 to about 30, preferably from about 20 to about 30, and most preferably from about 25 to about 30%, by weight cesium on an elemental basis, based on the total weight of the final zeolite catalyst composition.

When rubidium is employed as the alkali metal, the modification is typically conducted to impart a rubidium content (e.g. by exchange) to the zeolite of typically from about 5 to about 25, preferably from about 10 to about 25, and most preferably from about 15 to about 25%, by weight rubidium on an elemental basis, based on the total weight of the final zeolite catalyst composition.

When potassium is employed as the alkali metal, the modification is conducted (e.g. by exchange) to impart a potassium content to the zeolite of typically from about 3 to about 16, preferably from about 6 to about 16, and most preferably from about 10 to about 16%, by weight potassium on an elemental basis, based on the total final zeolite catalyst composition.

The preferred alkali metal is cesium. However, exchanges of sodium for Cs above about 65% normally are difficult to achieve from a practical standpoint because of the large size of the Cs atom. Cesium is more basic than K or Rb, all of which are more basic than Na. Moreover, the basicity of the catalyst is sought to be increased by alkali metal exchange, and it is preferred to maximize the Cs content to achieve this purpose. However, it has been found that the basicity of a Cs exchanged zeolite can be further enhanced by effecting initial exchange of sodium with K and/or Rb prior to Cs exchange since these former metals are smaller and fit into the zeolite structure more readily than Cs. Thus, a preferred embodiment is to effect partial exchange of Na with K and/or Rb prior to a cesium exchange to impart K and/or Rb contents within the ranges hereinabove described. Such partial exchanges will result, in an X-zeolite, in a sodium content in the zeolite of typically from about 0.5 to about 4.0, preferably from about 0.5 to about 2.0, and most preferably from about 0.5 to about 1%, by weight Na on an elemental basis, based on the total weight of the zeolite prior to modification, the remainder of the cationic sites in the zeolite preferably being occupied by the K and/or Rb cations. The K and/or Rb exchange is then preferably followed by the Cs exchange wherein the Na, K and/or Rb is exchanged for Cs to impart a cesium content in the amounts described above. In this way the maximum basicity associated with Cs described above can be imparted while further enhancing the basicity of cationic sites inaccessible to the Cs ions. To facilitate alkali metal or Group M metal exchange, some of the Na ions in the zeolite can be partially replaced initially with hydrogen ions. The hydrogen ions are more readily displaced by the alkali and Group M metal ions than sodium ions. This replacement may be accomplished by treatment of the zeolite with a fluid medium containing a hydrogen ion or an ion capable of conversion to a hydrogen ion. Inorganic and organic acids represent the source of hydrogen ions, whereas ammonium compounds are representative of the cations capable of conversion to hydrogen ions. Care should be taken to assure that all of the hydrogen ions so introduced in place of sodium are eventually replaced with the alkali or Group M metals since the protons can undesirably reduce the basicity of the catalyst.

The B and/or P components serve to improve the activity (e.g. conversion) of the catalyst, when present in conjunction with alkali and Group M metals, and are employed in amounts effective to achieve such improvements relative to their absence.

Thus, while any effective amount of the B and/or P components may be incorporated into the zeolite it is contemplated that such effective amounts constitute typically from about 0.001 to about 4, preferably from about 0.002 to about 0.5, and most preferably from about 0.002 to about 0.1%, by weight of each of said components on an elemental basis, based on the total weight of the zeolite catalyst containing said components.

The Group M metal serves to enhance the selectivity of the alkali metal (i.e., Cs, K, Rb) and B and/or P modified zeolite to styrene relative to its absence. This effect is most pronounced when Cs is present in the zeolite. Thus, while any effective amount of the Group M metal can be incorporated into the zeolite, it is contemplated that such effective amounts be sufficient to provide a respective gram atom ratio of alkali metal (e.g. Cs) to the Group M metal in the catalyst of from about 1:1 to about 100:1, preferably from about 1:1 to about 50:1, and most preferably from about 1:1 to about 30:1. Alternatively, the amount of Group M metal incorporated into the zeolite can be expressed as a weight fraction of the total catalyst. Accordingly, the Group M metal is incorporated into the zeolite in an amount of from about 0.01 to about 5, preferably from about 0.05 to about 2, and most preferably from about 0.1 to about 1% by weight on an elemental basis based on the total catalyst weight.

The residual sodium ion content in the zeolite after completion of the ion exchanges typically will vary from about 0.5 to about 4.5%, preferably from about 0.5 to about 2.5% and most preferably from about 0.5 to about 1.0% by weight on an elemental basis, based on the total zeolite composition weight.

To avoid loss of the modifying components by leaching or exchange, it is generally preferred to avoid excessive washing or similar procedures subsequent to modification. Also it is undesirable to subject the catalyst to treatments known to cause loss of cations by exchange with hydrogen or other ions.

The modified zeolite catalyst is generally dried following impregnation procedures typically at temperatures of from about 80 to about 150, preferably from about 90 to about 120, and most preferably from about 100° to about 110° C., although drying is optional.

The modified zeolite composition is preferably calcined prior to use. Calcination can be conducted in a separate step or in-situ in the reactor and involves heating the modified zeolite catalyst composition.

Calcination is a heat treatment wherein the solid state structure of the catalyst is fixed. Chemical elements composing the catalyst composition are fixed in a matrix.

Accordingly, calcination is conducted at temperatures of typically from about 300 to about 600, preferably from about 400 to about 500, and most preferably from about 400° to about 450° C., for a period of typically from about 1 to about 24, preferably from about 2 to about 16, and most preferably from about 4 to about 16 hours. In conducting calcination, the catalyst is typically heated to the selected calcination temperature(s), at a rate of preferably not greater than about 10° C./min, and most preferably not greater than about 5° C./min.

The atmosphere under which calcination is conducted typically comprises any one or more of air, nitrogen, argon, helium and the like. Although not essential, it is preferred that the calcination atmosphere be passed as a moving stream over the catalyst composition.

The modified zeolites described herein after calcination typically will possess an average pore size of typically from about 6 to about 15, and most preferably from about 8 to about 13 (e.g. 10 to 13) angstroms in diameter.

The modified zeolite catalyst is adaptable to use in the various physical forms in which catalysts are commonly used as particulate material in a contact bed, or a coating material on monolithic structures generally being used in a form to provide high surface area. The catalyst, can if desired, be composited with various catalyst binder or support materials which do not adversely affect the catalyst or the reactions in which the catalyst is to be employed.

The modified zeolite compositions described herein exhibit unexpected activity and styrene selectivity vis-a-vis the side chain alkylation of toluene. Accordingly, conditions generally used in side chain alkylation of toluene with methanol in the presence of conventional zeolite catalysts can be employed. The particular reaction conditions selected will be influenced by such considerations as activity, and temperature stability of the catalyst, desired conversion, and attainable product selectivity.

The toluene alkylation reaction is preferably carried out in the vapor phase and under the influence of heat, although liquid phase reaction can also be employed. The temperature range under which the reaction can be carried out typically will range from about 300 to about 550, preferably from about 380 to about 480, and most preferably from about 400° to about 450° C.

Pressure is not critical in the alkylation process of this invention although it is known that very high pressures can suppress methanol decomposition and thereby improve selectivity. Thus, the reaction may be carried out at subatmospheric, atmospheric, or superatmospheric pressures as desired although the pressure will typically be selected in conjunction with the reaction temperature to assure the reactants are in the vapor phase when contacting the catalyst. It will be generally preferred, however, to conduct the reaction at pressures of typically from about 1 to about 70, preferably from about 25 to about 70, and most preferably from about 50 to about 70 atmospheres.

The process of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactants and the modified zeolite composition. The reactants toluene or toluene derivatives and methanol will generally be heated and introduced into the reactor as a vapor. However, the reactant may be introduced to the reactor as a liquid and then vaporized.

The reaction time for the contact of the reactants with the modified zeolite composition in the present invention may be selected from a broad operable range which may vary from about 0.4 to about 8, preferably from about 1 to about 5, and most preferably from about 2 to about 4 seconds. The reaction time may be defined as the length of time in seconds which the reactant gases measured under reaction conditions are in contact with the modified zeolite composition in the reactor. The selected reaction time may vary depending upon the reaction temperature and the desired toluene conversion level. At higher temperatures and lower toluene conversion levels, shorter contact times are required. For example, the reactant feedstream may be passed over the catalyst at a gas hourly space velocity (GHSV) of typically from about 450 to about 9000, preferably from about 720 to about 3600, and most preferably from about 900 to about 1800 $hr^{-1}$.

The reactant feedstream will typically comprise toluene and methanol. The respective amounts of toluene and methanol supplied to the reactor may be specified as a mole ratio of the same. On this basis the mole ratio of toluene:methanol supplied to the reaction zone is typically controlled to be from about 1:0.05 to about 1:20, preferably from about 1:0.1 to about 1:10 (e.g. 1:2 to about 1:10), and most preferably from about 1:0.25 to about 1:2 (e.g. 1:2 to about 1:5). It is an advantage of the present invention that amounts of methanol in excess of stoichiometric amounts (i.e. toluene:methanol mole ratio of 1:1) can be employed without sacrificing styrene yield to the extent which occurs in the absence of the Group M metal in the catalyst.

In addition to the aforedescribed reactants, other inert diluent gases such as nitrogen, argon, carbon dioxide, helium and the like are also preferably introduced into the reactor. Such inert gases may be introduced to the process alone or may be combined with the other materials of feed. Preferably the inert gas is introduced to the reaction zone in a manner sufficient to achieve a mole ratio of toluene:inert gas therein of typically from about 0.4:1 to about 5:1, preferably from about 0.5:1 to about 2:1, and most preferably from about 0.75:1 to about 2:1. The preferred inert gas is nitrogen.

While the present invention is described in conjunction with the side chain alkylation of toluene, methyl substituted derivatives of toluene can also be employed for such side chain alkylation thereof. Thus, the hydrocarbon feed source which can be employed in the process of the present invention comprises at least one compound represented by the structural formula:

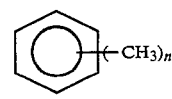

(I)

wherein n is a number from 1 to 6, preferably 1 to 4, most preferably 1 to about 3, (e.g. 2). Representative examples of such hydrocarbon feed sources suitable for alkylation in addition to toluene, include o-xylene, m-xylene, p-xylene, 1,3,5-trimethylbenzene, 1,2,4-trimethylbenzene, 1,2,4,6-tetramethylbenzene, hexamethylbenzene, pentamethylbenzene and the like. The most preferred toluene derivatives are the xylenes.

Generally, when a hydrocarbon feed source for alkylation other than toluene is employed the alkylated product will be the appropriate methyl substituted styrene or ethylbenzene products, e.g. the methyl groups in excess of 1 are carried along and remain uneffected by the alkylation reactions.

The term "toluene derivative" is therefore defined herein to be at least one compound represented by formula I wherein n is between 2 and 6.

Furthermore, while the present invention has been described in connection with methanol as the alkylating agent, other alkylating agents may be employed under the same range of conditions. Thus, formaldehyde and/or various forms or sources of formaldehyde can be employed as the alkylating agent including trioxane, methylal, paraformaldehyde, or commercial formaldehyde solutions, such as Formcel formaldehyde solution (55% formaldehyde, 10% water and the balance methanol). The term "alkylating agent" as defined herein is therefore intended to describe any one or more of the abovedescribed materials in addition to methanol.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples and unless otherwise specified, selectivity and conversion are calculated as follows:

$$\% \text{ selectivity} = \frac{\text{moles of desired product}}{\text{moles of toluene in feed}} \times 100$$

$$\% \text{ conversion} = \frac{\text{moles of toluene in feed reacted}}{\text{moles of toluene in feed}} \times 100$$

$$\% \text{ yield} = \frac{\text{selectivity (\%)} \times \text{conversion (\%)}}{100}$$

EXAMPLES 1 TO 4

A cesium-boron-phosphorus modified zeolite composition was prepared as follows by a multiple ion-exchange technique as follows:

Part A

An aqueous cesium hydroxide solution was prepared by dissolving 46.69 g of $CsOH.XH_2O$ (83%) (0.26 moles CsOH) in 400 ml of deionized water at room temperature (20° C.). The resulting solution was divided into four 100 ml portions which were successively admixed (in the absence of stirring) with a 50 g sample of Davison 4–8 mesh beads of 13X zeolite to form four slurries. Each slurry was allowed to soak at 90° C. for different periods, namely, 16; 2; 2; and 2 hours respectively, and the liquid portion of each solution was removed from the zeolite before adding the next portion.

Part B

A second solution containing 22 g $CsOH.XH_2O$ (83%) and 4 g $BPO_4$ dissolved in 400 ml of deionized water was then prepared. A portion of this solution (100 ml) was then admixed with the zeolite, treated in accordance with Part A to form a slurry which was heated at 90° C. for 2 hours. The liquid portion of the slurry was removed, and the remaining 300 ml portion of the exchange solution admixed to form another slurry with the zeolite, at 90° C. for 16 hours. The liquid contents of this slurry were removed and the CsBP-X zeolite washed with 500 ml water and dried at 110° C. for 7 hours.

Part C

The partially modified zeolite prepared in accordance with Part B was divided into 4 samples and each sample was further modified by exchange with cations of one of Mn, Fe, Cu and Zn. Accordingly, four separate solutions were prepared by dissolving $Mn(Ac)_2.4H_2O$ (Solution 1), $Fe(Ac)_2$ (Solution 2) $Cu(NO_3)_2.3H_2O$ (Solution 3) or $Zn(NO_2)_2.6H_2O$ (Solution 4) in 40 ml of deionized water, Ac representing acetate. The amount of each Group M metal salt dissolved in each solution is sufficient to obtain therein 0.2 wt.% of each Group M metal on an elemental basis, based on the total weight of zeolite from Part B to which the solution was to be added.

Each of Solutions 1 to 4 was then admixed with 5 g of the CsBP-X zeolite from Part B at 20° C. for 16 hours to form a slurry. The slurry was dried in air at 110° C. for 7 hours.

Part D

Five cc of each of the dried modified zeolite samples from Solutions 1 to 4 were placed into a 40 cc vertical quartz reactor (0.5" O.D., and ⅜" I.D.) stoppered at the bottom with glass wool. About 15 cc of the reactor above the catalyst was filled with glass wool which serves as a preheating zone. Heat was supplied to the reactor with a tubular furnace. Each catalyst sample was calcined in-situ by passing $N_2$ gas through the reactor at a rate of 200 cc/min. The temperature of the reactor was 430° C. during calcination. Calcination times for each sample are reported in Table 1. Upon completion of calcination, a liquid mixture of toluene and methanol having a toluene:methanol mole ratio thereof of 1:7.5 was combined with a nitrogen carrier gas in an amount sufficient to achieve a toluene:$N_2$ mole ratio in the feed of 1:2 (i.e. $N_2$ was fed at a rate of 15 cc/min). The resulting toluene/methanol/$N_2$ feed was passed through the top of the reactor, maintained at 425° C., for each Example, at a rate sufficient to achieve a contact time with each catalyst sample of 4 seconds at STP. Each effluent stream was passed through a condenser and sample collectors and the liquid effluent collected for 60 minutes and analyzed by gas chromatography. The results of the analysis are summarized at Table 1.

COMPARATIVE EXAMPLE 1

A sample of the CsBP-X zeolite prepared in accordance with Part C of Examples 1–4, was calcined and tested in accordance with Part D of Examples 1–4 and the results summarized at Table 1.

DISCUSSION OF RESULTS

From the data of Table 1, it can be seen that in the absence of a Group M cation, while toluene conversion is 25% the styrene yield is only 2.8% (Comp. Ex. 1). In contrast the presence of the Group M metal in all cases substantially improves the styrene yield, and in Example 3 such improvement is more than triple the styrene yield of Comp. Ex. 1. Such improvements in styrene yield are obtained at the same or higher toluene conversions as the control. All of the toluene conversions in Table 1 are more than 3 times the maximum toluene conversion obtainable in U.S. Pat. No. 4,140,726 in view of the higher methanol content in the Examples and Comparative Example 1 herein.

TABLE 1

| Example No. | Group M Metal Cation in CsBP—X Zeolite | Calcination Time (hr.) | Toluene Conv. (%) | EB + S Selectivity (%) | Styrene Selectivity (%) | EB + S Yield (%) | Styrene Yield (%) |
| --- | --- | --- | --- | --- | --- | --- | --- |
| 1 | Mn | 2 | 25 | 80 | 15 | 20.0 | 3.8 |
| 2 | Fe | 2 | 25 | 75 | 14 | 18.7 | 4.8 |
| 3 | Cu | 16 | 26 | 80 | 33 | 20.8 | 8.6 |
| 4 | Zn | 2 | 28 | 72 | 21 | 20.2 | 5.8 |
| Comp. Ex. 1 | None | 16 | 25 | 84 | 11 | 21.0 | 2.8 |

EB = ethylbenzene
S = styrene

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for alkylating toluene or toluene derivative with at least one alkylating agent which comprises reacting said alkylating agent with at least one compound represented by the structural formula:

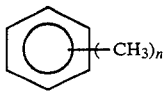

(I)

wherein n is a number which can vary from 1 to 6, said reaction being conducted in the presence of a catalyst composition comprising a crystalline aluminosilicate zeolite of the faujasite structure with a $SiO_2:Al_2O_3$ mole ratio of from about 2 to about 8 and having present therein (1) at least one alkali metal selected from the group consisting of Cs, K, and Rb; (2) at least one metal selected from the Group of M metals consisting of Mn, Fe, Cu, and Zn; and (3) at least one member selected from the group consisting of boron and phosphorus in a manner and under conditions sufficient to form a product comprising at least one compound represented by the structural formulae:

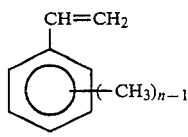

(II)

and

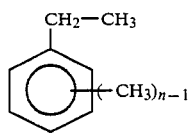

(III)

wherein n is a number which corresponds in value to that employed for n in structural formula I.

2. The process of claim 1 wherein methanol is reacted with toluene to form a product comprising styrene.

3. The process of claim 1 wherein methanol is reacted with p-xylene to form p-methylstyrene.

4. The process of claim 2 wherein said reaction is conducted in the vapor phase by contacting a feed gas mixture comprising toluene and methanol, present in said gas mixture at a respective mole ratio of from about 1:0.05 to about 1:20, with said zeolite catalyst composition at a reaction temperature of from about 300° to about 550° C.

5. The process of claim 4 wherein said toluene:methanol mole ratio in said feed gas is from about 1:2 to about 1:10.

6. The process of claim 4 wherein said toluene:methanol mole ratio in said feed gas is from about 1:2 to about 1:5.

7. The process of claim 4 wherein said feed gas mixture contains an inert diluent gas.

8. The process of claim 7 wherein the inert diluent gas is nitrogen which is present in said feed gas mixture at a toluene:$N_2$ mole ratio of from about 0.4:1 to about 5:1.

9. The process of claim 1 wherein in said catalyst composition the alkali metal and Group M metal are present as cations within said zeolite.

10. The process of claim 9 wherein in said catalyst composition boron is present within said zeolite as a cation.

11. The process of claim 1 wherein in said catalyst composition cesium is present within said zeolite as a cation.

12. The process of claim 11 wherein in said catalyst composition boron and phosphorus are present within said zeolite.

13. The process of claim 11 wherein in said catalyst composition manganese is present in said zeolite.

14. The process of claim 11 wherein in said catalyst composition iron is present in said zeolite.

15. The process of claim 11 wherein in said catalyst composition copper is present in said zeolite.

16. The process of claim 11 wherein in said catalyst composition zinc is present in said zeolite.

17. The process of claim 11 wherein in said catalyst composition the zeolite is of the X- or Y-type having a cesium content of from about 10 to about 30% by weight on an elemental basis based on the total weight of the catalyst composition.

18. The process of claim 11 wherein in said catalyst composition the Group M metal is present in said zeolite in an amount sufficient to provide therein a gram atom ratio of cesium:Group M metal of from about 1:1 to 100:1.

19. The process of claim 11 wherein in said catalyst composition the zeolite is of the X-type.

20. The process of claim 11 wherein in said catalyst composition boron and phosphorus are present in said zeolite in an amount of from about 0.001 to about 4% by weight of each of said components on an elemental basis, based on the total weight of the catalyst composition.

21. The process of claim 11 wherein in said catalyst composition the sodium content of the zeolite is from about 0.5 to about 4.5% by weight on an elemental basis, based on the total catalyst composition weight.

* * * * *